United States Patent
Rapold et al.

(10) Patent No.: US 10,071,036 B2
(45) Date of Patent: *Sep. 11, 2018

(54) DYEING PROCESS USING A MIXTURE COMPRISING A BRANCHED $C_6$-$C_{12}$ POLYOL, OBTAINED FROM AN AEROSOL DEVICE, AND DEVICE THEREFOR

(71) Applicant: L'OREAL, Paris (FR)

(72) Inventors: Philippe Rapold, Paris (FR); Caroline Goget, Paris (FR); Delphine Allard, Paris (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/396,943

(22) PCT Filed: Apr. 22, 2013

(86) PCT No.: PCT/EP2013/058314
§ 371 (c)(1),
(2) Date: Oct. 24, 2014

(87) PCT Pub. No.: WO2013/160262
PCT Pub. Date: Oct. 31, 2013

(65) Prior Publication Data
US 2015/0335545 A1    Nov. 26, 2015

Related U.S. Application Data

(60) Provisional application No. 61/663,137, filed on Jun. 22, 2012.

(30) Foreign Application Priority Data

Apr. 24, 2012 (FR) .................................. 12 53740

(51) Int. Cl.
*A61Q 5/10* (2006.01)
*A61K 8/34* (2006.01)
*A61K 8/41* (2006.01)
*A61K 8/46* (2006.01)
*A61K 8/92* (2006.01)
*A61K 8/04* (2006.01)
*A61K 8/22* (2006.01)

(52) U.S. Cl.
CPC .............. *A61K 8/345* (2013.01); *A61K 8/046* (2013.01); *A61K 8/22* (2013.01); *A61K 8/347* (2013.01); *A61K 8/411* (2013.01); *A61K 8/463* (2013.01); *A61K 8/92* (2013.01); *A61Q 5/10* (2013.01); *A61K 2800/4324* (2013.01); *A61K 2800/88* (2013.01); *A61K 2800/882* (2013.01)

(58) Field of Classification Search
CPC .......... A61K 8/345; A61K 8/411; A61K 8/92; A61K 2800/4324; A61K 2800/882; A61Q 5/10
USPC .............................................. 8/405; 132/208
See application file for complete search history.

(56) References Cited

U.S. PATENT DOCUMENTS

| 3,915,921 A | 10/1975 | Schlatzer, Jr. |
| 4,003,699 A | 1/1977 | Rose et al. |
| 4,137,180 A | 1/1979 | Naik et al. |
| RE30,199 E | 1/1980 | Rose et al. |
| 4,509,949 A | 4/1985 | Huang et al. |
| 4,874,554 A | 10/1989 | Lange et al. |
| 5,061,289 A | 10/1991 | Clausen et al. |
| 5,089,578 A | 2/1992 | Valint et al. |
| 5,380,340 A | 1/1995 | Neunhoeffer et al. |
| 5,534,267 A | 7/1996 | Neunhoeffer et al. |
| 5,663,366 A | 9/1997 | Neunhoeffer et al. |
| 5,766,576 A | 6/1998 | Lowe et al. |
| 5,863,300 A | 1/1999 | Audousset et al. |
| 6,099,592 A | 8/2000 | Vidal et al. |
| 6,120,780 A | 9/2000 | Dupuis et al. |
| 6,284,003 B1 | 9/2001 | Rose et al. |
| 6,338,741 B1 | 1/2002 | Vidal et al. |
| 6,645,258 B2 | 11/2003 | Vidal et al. |
| 6,730,789 B1 | 5/2004 | Birault et al. |
| 6,822,039 B1 | 11/2004 | Monfreux-Gaillard et al. |

(Continued)

FOREIGN PATENT DOCUMENTS

| DE | 2359399 A1 | 6/1975 |
| DE | 3843892 A1 | 6/1990 |

(Continued)

OTHER PUBLICATIONS

International Search Report and Written Opinion for PCT/EP2013/058314, dated Jun. 3, 2014.
Porter, M.R., "Handbook of Surfactants," published by Blackie & Son (Glasgow and London), 1991, pp. 116-178.
Todd, Charles, et al., "Volatile Silicone Fluids for Cosmetic Formulations," Cosmetics and Toiletries, vol. 91, Jan. 1976, pp. 29-32.
English language Abstract for DE102009055125 (May 5, 2011).
English language Abstract for EP 0770375 (May 2, 1997).
English language Abstract for FR 2886136 (EP1728500) (Dec. 1, 2006).
English language Abstract for FR 2926983 (Aug. 7, 2009).
English language Abstract for JP 05-163124 (Jun. 29, 1993).
English language Abstract for DE1020060055436 (Oct. 11, 2007).
English language Abstract for DE102007056935 (May 28, 2009).
English language Abstract for EP 2062616 (May 27, 2009).

(Continued)

*Primary Examiner* — Eisa B Elhilo
(74) *Attorney, Agent, or Firm* — The Marbury Law Group, PLLC

(57) ABSTRACT

The present invention relates to a process for dyeing keratin fibers in which a mixture is applied, this mixture being obtained from: •a dye composition comprising at least one oxidation dye precursor and at least a liquid fatty substance, and •an oxidizing composition comprising at least one chemical oxidizing agent, •at least one of the compositions being dispensed from a pressurized container, •the mixture of the two compositions comprising at least one branched $C_6$-$C_{12}$ polyol, and also to equipment suitable for performing this process.

19 Claims, No Drawings

(56) References Cited

U.S. PATENT DOCUMENTS

| | | | |
|---|---|---|---|
| 7,141,282 | B2 | 11/2006 | Demars et al. |
| 7,153,331 | B2 | 12/2006 | Desenne et al. |
| 7,204,858 | B2 | 4/2007 | Desenne et al. |
| 7,402,180 | B2 | 7/2008 | Vuarier et al. |
| 7,722,682 | B2 | 5/2010 | Cottard et al. |
| 7,933,737 | B2 | 4/2011 | Gross et al. |
| 8,114,170 | B2 | 2/2012 | Goget et al. |
| 2002/0050013 | A1 | 5/2002 | Vidal et al. |
| 2003/0019051 | A9 | 1/2003 | Vidal et al. |
| 2003/0074747 | A1* | 4/2003 | Vuarier ............... A61Q 5/10 8/405 |
| 2003/0124079 | A1 | 7/2003 | Mougin et al. |
| 2003/0182734 | A1 | 10/2003 | Desenne et al. |
| 2003/0192134 | A1 | 10/2003 | Desenne et al. |
| 2004/0068805 | A1 | 4/2004 | Fishman |
| 2004/0141943 | A1 | 7/2004 | Mougin et al. |
| 2004/0194229 | A1 | 10/2004 | Lagrange |
| 2004/0209019 | A1 | 10/2004 | Demars et al. |
| 2005/0226838 | A1 | 10/2005 | Krause et al. |
| 2006/0248662 | A1 | 11/2006 | Legrand |
| 2009/0247650 | A1 | 10/2009 | Mougin et al. |
| 2010/0154140 | A1 | 6/2010 | Simonet et al. |
| 2010/0158839 | A1 | 6/2010 | Braida-Valerio et al. |
| 2010/0162492 | A1 | 7/2010 | Hercouet et al. |
| 2010/0236570 | A1* | 9/2010 | Fujinuma ............ A61Q 5/10 132/208 |
| 2011/0146007 | A1 | 6/2011 | Goget et al. |
| 2012/0192889 | A1 | 8/2012 | Schmelz et al. |
| 2018/0078485 | A1 | 3/2018 | Rapold et al. |

FOREIGN PATENT DOCUMENTS

| | | |
|---|---|---|
| DE | 4133957 A1 | 4/1993 |
| DE | 19543988 A1 | 5/1997 |
| DE | 102006055436 A1 | 10/2007 |
| DE | 102007056935 A1 | 5/2009 |
| DE | 102009055125 A1 | 5/2011 |
| EP | 0173109 A1 | 3/1986 |
| EP | 0503853 A1 | 9/1992 |
| EP | 0750899 A1 | 1/1997 |
| EP | 0770375 A1 | 5/1997 |
| EP | 0815828 A1 | 1/1998 |
| EP | 1279395 A1 | 1/2003 |
| EP | 1323409 A1 | 7/2003 |
| EP | 1645264 A1 | 4/2006 |
| EP | 2062616 A1 | 5/2009 |
| EP | 2198849 A1 | 6/2010 |
| EP | 2204157 A1 | 7/2010 |
| EP | 2283803 A1 | 2/2011 |
| EP | 2338571 A1 | 6/2011 |
| FR | 2048629 A5 | 3/1971 |
| FR | 2733749 A1 | 11/1996 |
| FR | 2801308 A1 | 5/2001 |
| FR | 2811993 A1 | 1/2002 |
| FR | 2886136 A1 | 12/2006 |
| FR | 2926983 A1 | 8/2009 |
| FR | 2940067 A1 | 6/2010 |
| GB | 1026978 A | 4/1966 |
| GB | 1153196 A | 5/1969 |
| GB | 1271331 A | 4/1972 |
| JP | 02-019576 | 1/1990 |
| JP | 05-163124 | 6/1993 |
| WO | 94/08969 A1 | 4/1994 |
| WO | 94/08970 A1 | 4/1994 |
| WO | 96/15765 A1 | 5/1996 |
| WO | 0031154 A1 | 6/2000 |
| WO | 0068282 A1 | 11/2000 |
| WO | 2006060569 A2 | 6/2006 |

OTHER PUBLICATIONS

Fonnum, G. et al., "Associative Thickeners. Part I: Synthesis, Rhelogy and Aggregation Behavior," Colloid & Polymer Science, 271, (1993), pp. 380-389.

International Search Report and Written Opinion for PCT/EP2013/058304, dated Jul. 31, 2014.

International Search Report and Written Opinion for PCT/EP2013/058306, dated Jul. 31, 2014.

International Search Report and Written Opinion for PCT/EP2013/058312, dated May 27, 2014.

International Search Report and Written Opinion for PCT/EP2013/058315, dated Jun. 2, 2014.

Kirk-Othmer's Encyclopedia of Chemical Technology, 3rd Edition, vol. 3, 1982, pp. 896-900.

Macgregor, E.A., et al., "Polymers in Nature," published by John Wiley & Sons, Chapter 6, (1980), pp. 240-328.

Microbial Polysaccharides, Kirk-Othmer Encyclopedia of Chemical Technology, Third Edition, vol. 15, pp. 439-458.

Morishima Y., "Self-Assembling Amphiphilic Polyelectrolytes and their Nanostructures," Chinese Journal of Polymer Science, vol. 18, No. 40, 2000, pp. 323-336.

Noda, Tetsuya et al.; "Solution Properites of Micelle Networks Formed by Nonionic Surfactant Moieties Covalently Bound to a Polyelectrolyte: Salt Effects on Rheological Behavior", 2000, ACS, Langmuir, vol. 16, No. 12, pp. 5324-5332.

Non-Final Office Action for co-pending U.S. Appl. No. 14/396,900, dated Apr. 7, 2015.

Non-Final Office Action for co-pending U.S. Appl. No. 14/396,926, dated Apr. 27, 2015.

Non-Final Office Action for co-pending U.S. Appl. No. 14/396,952, dated Apr. 30, 2015.

Non-Final Office Action for co-pending U.S. Appl. No. 14/396,966, dated Apr. 7, 2015.

Tetsuya Noda et al, "Micelle Formation of Random Copolymers of Sodium 2-(Acrylamido)-2- methylpropanesulfonate and a Nonionic Surfactant Macromonomer in Water as Studied by Fluorescence and Dynamic Light Scattering," Macromolecules, vol. 33, pp. 3694-3704 (2000).

Tetsuya Noda et al., "Stimuli-Responsive Amphiphilic Copolymers of Sodium 2-(Acrylamino)-2-Methylpropanesulfonate and Associative Macromonomers," Polymer Preprints, vol. 40, No. 2, pp. 220-221 (1999).

Final Office Action for co-pending U.S. Appl. No. 14/396,900, dated Nov. 12, 2015.

Non-Final Office Action for co-pending U.S. Appl. No. 14/396,900, dated May 23, 2016.

Final Office Action for co-pending U.S. Appl. No. 14/396,926, dated Jan. 12, 2016.

Final Office Action for co-pending U.S. Appl. No. 14/396,952, dated Jan. 13, 2016.

Final Office Action for co-pending U.S. Appl. No. 14/396,966, dated Nov. 23, 2015.

Non-Final Office Action for co-pending U.S. Appl. No. 14/396,966, dated May 11, 2016.

Non-Final Office Action for co-pending U.S. Appl. No. 14/396,952, dated Aug. 8, 2016.

Final Office Action for co-pending U.S. Appl. No. 14/396,966 (dated Nov. 28, 2016).

Notice of Allowance for copending U.S. Appl. No. 14/396,900, dated Jan. 27, 2017 (now U.S. Pat. No. 9,662,290).

Corrected Notice of Allowance for copending U.S. Appl. No. 14/396,900, dated Feb. 9, 2017 (now U.S. Pat. No. 9,662,290).

Final Office Action for copending U.S. Appl. No. 14/396,926, dated Mar. 2, 2017.

* cited by examiner

DYEING PROCESS USING A MIXTURE COMPRISING A BRANCHED $C_6$-$C_{12}$ POLYOL, OBTAINED FROM AN AEROSOL DEVICE, AND DEVICE THEREFOR

CROSS REFERENCE TO RELATED APPLICATIONS

This is a national stage application of PCT/EP2013/058314, filed internationally on Apr. 22, 2013, which claims priority to U.S. Provisional Application No. 61/663,137, filed on Jun. 22, 2012, as well as French Application No. 1253740, filed Apr. 24, 2012, all of which are incorporated herein by their entireties.

The present invention relates to a process for dyeing the hair using a mixture comprising at least one branched $C_6$-$C_{12}$ polyol, the said mixture being obtained from two compositions, at least one of which is conditioned in a pressurized container, and also to a device suitable for performing this process.

Among the methods for dyeing human keratin fibres, such as the hair, mention may be made of oxidation dyeing or permanent dyeing. More particularly, this form of dyeing uses one or more oxidation dyes, usually one or more oxidation bases optionally combined with one or more couplers.

In general, oxidation bases are chosen from ortho- or para-phenylenediamines, ortho- or para-aminophenols and heterocyclic compounds. These oxidation bases are colourless or weakly coloured compounds which, when combined with oxidizing products, can give access to coloured entities.

Quite often, the shades obtained with these oxidation bases are varied by combining them with one or more couplers, these couplers being chosen especially from aromatic meta-diamines, meta-aminophenols, meta-diphenols and certain heterocyclic compounds, such as indole compounds.

The variety of the molecules used as oxidation bases and couplers allows a wide range of colours to be obtained.

Permanent dyeing processes thus consist in using with the dye composition an aqueous composition comprising at least one oxidizing agent such as hydrogen peroxide, under alkaline pH conditions in the vast majority of cases. The alkaline agent conventionally used is aqueous ammonia or other alkaline agents, such as alkanolamines.

Dye compositions may take various forms such as lotions, gels, emulsions, creams or foams.

These compositions, in particular compositions comprising oxidation dyes, are obviously oxidation-sensitive and consequently contain reducing agents or antioxidants. This oxidation-preventing action is also reinforced by means of the inert atmosphere that is occasionally used during the conditioning of these compositions.

The difficulty encountered with compositions of this type results, precisely, from their oxidation sensitivity. Specifically, during their use, they come into contact with atmospheric oxygen, which thus obliges them to be used quickly. If this is not done, the compositions become unusable after storage and are lost.

Compositions which are conditioned in pressurized containers that can prevent the composition from coming into contact with air during their use are known in the field of hair dyeing, as is described, for example, in US 2010/0236570 or FR 2 048 629.

However, the coverage of the hair, in particular of grey hair, still remains to be improved, as does the galenical quality of the product obtained from the pressurized container.

There is an ongoing need to develop oxidation dye compositions in foam form which are easy to prepare and to apply and which remain sufficiently stable over time, while at the same time maintaining efficient dyeing properties, especially in terms of coverage of the hair, in particular of grey hair, but also in terms of the intensity, homogeneity and chromaticity of the coloration obtained.

This aim and others are achieved by the present invention, one subject of which is a process for dyeing keratin fibres in which a mixture is applied to the said fibres, this mixture being obtained from:
 a dye composition comprising at least one oxidation dye precursor and at least a liquid fatty substance, and
 an oxidizing composition comprising at least one chemical oxidizing agent,
 at least one of the compositions being dispensed from a pressurized device,
 the mixture of the two compositions comprising at least one branched $C_6$-$C_{12}$ polyol.

The invention also relates to a device that is suitable for performing the process according to the invention, comprising:
 a first container containing a dye composition comprising at least one oxidation dye precursor and at least a liquid fatty substance, and
 a second container containing an oxidizing composition comprising at least one chemical oxidizing agent,
 at least one of the containers being pressurized, and preferably both the containers being pressurized;
 a means for dispensing the compositions;
 the mixture of the two compositions comprising at least one branched $C_6$-$C_{12}$ polyol.

Preferably, the composition used in the process according to the invention is in the form of a foam that is particularly pleasant to apply.

It has a light, airy texture, which makes it particularly pleasant to use. The qualities of the foam are sufficiently long-lasting to enable uniform application of the dye product, without running.

The composition of the invention makes it possible to retain dyeing properties, such as strength of the colour, resistance to external agents (shampooing, perspiration, light) and selectivity, and most particularly coverage of grey hair.

Other characteristics and advantages of the invention will emerge more clearly on reading the description and the examples that follow.

In the text hereinbelow, and unless otherwise indicated, the limits of a range of values are included in that range. The term "at least one" associated with an ingredient of the composition means "one or more".

The terms "oxyalkylenated", "oxyethylenated", "oxypropylenated" and "glycerolated" cover, respectively, mono- or poly-oxyalkylenated, oxyethylenated, oxypropylenated or glycerolated compounds, unless otherwise mentioned.

Unless otherwise indicated, the contents of the ingredients present in the compositions are indicated without taking into account the content of propellant gas(es).

The human keratin fibres treated via the process according to the invention are preferably the hair.

Branched Polyol

As indicated previously, the mixture used in the present invention comprises at least one branched $C_6$-$C_{12}$ polyol.

More particularly, the branched polyol(s) correspond to the following formula (I):

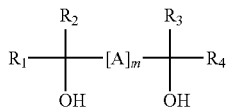

in which:
R$_1$, R$_2$, R$_3$ and R$_4$ denote, independently of each other, a hydrogen atom, a linear C$_1$-C$_6$ alkyl radical, a branched C$_3$-C$_6$ alkyl radical or a C$_1$-C$_6$ monohydroxyalkyl or polyhydroxyalkyl radical;

A denotes an optionally mono- or polyhydroxylated linear C$_1$-C$_{10}$ and preferably C$_1$-C$_6$ alkylene radical, or a branched C$_3$-C$_{10}$ and preferably C$_3$-C$_6$ alkylene radical, the said radical optionally being interrupted with 1 to 3 oxygen atoms;

m is 0 or 1;

the radicals R$_1$, R$_2$, R$_3$, R$_4$ and A, where appropriate, being such that the compound of formula (I) is branched and comprises 6 to 12 carbon atoms.

According to a first variant, the branched polyol(s) are such that m is zero, R$_1$, R$_2$, R$_3$ and R$_4$ denoting, independently of each other, a hydrogen atom, an optionally mono- or polyhydroxylated linear C$_1$-C$_6$ or branched C$_3$-C$_6$ alkyl radical, at least one of the radicals being branched or the radicals R$_1$ and R$_2$ and/or the radicals R$_3$ and R$_4$ being other than hydrogen; the radicals being such that the compound of formula (I) is branched and the number of carbon atoms ranging from 6 to 12.

Preferably, the polyol corresponding to this variant is pinacol.

According to a second variant, the branched polyol(s) are such that m is 1, R$_1$, R$_2$, R$_3$ and R$_4$ denoting, independently of each other, a hydrogen atom, an optionally mono- or polyhydroxylated linear C$_1$-C$_6$ or branched C$_3$-C$_6$ alkyl radical, A representing an optionally branched C$_1$-C$_6$ alkylene group optionally interrupted with one or more oxygen atoms, the radicals being such that the compound of formula (I) is branched and the number of carbon atoms ranging from 6 to 12.

In this variant, more preferentially, A is not interrupted with one or more oxygen atoms.

Preferably, the polyol(s) corresponding to this variant are chosen from 3-methyl-1,3,5-pentanetriol, 3-methyl-1,5-pentanediol and hexylene glycol (2-methyl-2,4-pentanediol), or mixtures thereof.

In one variant of the invention, the polyols are diols.

For the compounds of formula (I), this means that the substituents R$_1$ to R$_4$ are not hydroxylated.

The polyols that are more particularly preferred according to the invention are hexylene glycol and 3-methyl-1,5-pentanediol or mixtures thereof. According to a particularly advantageous embodiment of the invention, the polyol is hexylene glycol.

More particularly, the content of branched polyol(s) represents from 0.1% to 50% by weight and preferably from 1% to 10% by weight, relative to the weight of the mixture.

The branched polyol(s) may be in the dye composition, in the oxidizing composition or in both compositions simultaneously.

Dye Composition

Dyes

The dye composition used in the process according to the invention comprises at least one oxidation dye precursor.

Oxidation bases and couplers may be used as oxidation dye precursors.

By way of example, the oxidation bases are chosen from para-phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,6-dioxaoctane and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

Among the heterocyclic bases that may be mentioned, for example, are pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases that are useful in the present invention are the 3-aminopyrazolo[1,5-a]pyridine oxidation bases or the addition salts thereof described, for example, in patent application FR 2 801 308. Mention may be made, by way of example, of pyrazolo[1,5-a]pyrid-3-ylamine, 2-(acetylamino)pyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol and the addition salts thereof.

Among the pyrimidine derivatives that may be mentioned are the compounds described, for example, in patents DE 2359399, JP 88-169571, JP 05-63124 and EP 0 770 375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and addition salts thereof, and tautomeric forms thereof, when a tautomeric equilibrium exists.

Among the pyrazole derivatives that may be mentioned are the compounds described in patents DE 3843892, DE 4133957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triamino-pyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and addition salts thereof. Use may also be made of 4,5-diamino-1-(β-methoxyethyl)pyrazole.

A 4,5-diaminopyrazole will preferably be used, and even more preferentially 4,5-diamino-1-(β-hydroxyethyl)pyrazole and/or a salt thereof.

Pyrazole derivatives that may also be mentioned include diamino-N,N-dihydropyrazolopyrazolones and especially those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-one, 2,3-Diamino-6,7-dihydro-1H,5H-pyrazolo[1,2-a]pyrazol-1-one and/or a salt thereof will preferably be used.

Use will preferably be made, as heterocyclic bases, of 4,5-diamino-1-(β-hydroxyethyl)pyrazole and/or 2,3-diamino-6,7-dihydro-1H,5H-pyrazolo[1,2-a]pyrazol-1-one and/or a salt thereof.

Among the couplers that may be used in the composition used in the process according to the invention, mention may be made especially of meta-phenylenediamines, meta-aminophenols, meta-diphenols, naphthalene-based couplers, heterocyclic couplers, for instance indole derivatives, indoline derivatives, sesamol and derivatives thereof, pyridine derivatives, pyrazolotriazole derivatives, pyrazolones, indazoles, benzimidazoles, benzothiazoles, benzoxazoles, 1,3-benzodioxoles and quinolines, and the addition salts of these compounds with an acid.

These couplers are more particularly chosen from 2,4-diamino-1-(β-hydroxyethyloxy)benzene, 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2-amino-4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2-amino-3-hydroxypyridine, 3,6-dimethylpyrazolo[3,2-c]-1,2,4-triazole and 2,6-dimethylpyrazolo[1,5-b]-1,2,4-triazole, the addition salts thereof with an acid, and mixtures thereof.

The addition salts of the oxidation bases and couplers are especially chosen from the addition salts with an acid such as the hydrochlorides, hydrobromides, sulfates, citrates, succinates, tartrates, lactates, tosylates, benzenesulfonates, phosphates and acetates.

The oxidation base(s) are each generally present in an amount of from 0.0001% to 10% by weight relative to the total weight of the composition, and preferably from 0.005% to 5% by weight relative to the total weight of the dye composition.

The coupler(s) each generally represent from 0.0001% to 10% by weight relative to the total weight of the composition, and preferably from 0.005% to 5% by weight relative to the total weight of the dye composition.

The dye composition used in the process according to the invention may contain synthetic or natural, cationic or nonionic, direct dyes.

Examples of particularly suitable direct dyes that may be mentioned include nitrobenzene dyes; azo direct dyes; azomethine direct dyes; methine direct dyes; azacarbocyanin direct dyes, for instance tetraazacarbocyanins (tetraazapentamethines); quinone and in particular anthraquinone, naphthoquinone or benzoquinone direct dyes; azine direct dyes; xanthene direct dyes; triarylmethane direct dyes; indoamine direct dyes; indigoid direct dyes; phthalocyanin direct dyes, porphyrin direct dyes and natural direct dyes, alone or as mixtures. In particular, mention may be made of direct dyes from among: azo; methine; carbonyl; azine; nitro (hetero)aryl; tri(hetero)arylmethane; porphyrin; phthalocyanine and natural direct dyes, alone or as mixtures.

When they are present, the direct dye(s) more particularly represent from 0.0001% to 10% by weight and preferably from 0.005% to 5% by weight relative to the total weight of the dye composition.

Alkaline Agent

According to a preferred variant of the invention, the dye composition comprises at least one alkaline agent.

This agent may be chosen from mineral or organic or hybrid alkaline agents, or mixtures thereof.

The mineral alkaline agent(s) are preferably chosen from aqueous ammonia, alkali carbonates or bicarbonates such as sodium or potassium carbonates and sodium or potassium bicarbonates, sodium hydroxide or potassium hydroxide, or mixtures thereof.

The organic alkaline agent(s) are preferably chosen from organic amines with a $pK_b$ at 25° C. of less than 12, preferably less than 10 and even more advantageously less than 6. It should be noted that it is the $pK_b$ corresponding to the function of highest basicity.

Mention may be made, as hybrid compounds, of the salts of the abovementioned amines with acids, such as carbonic acid or hydrochloric acid.

The organic alkaline agent(s) are chosen, for example, from alkanolamines, oxyethylenated and/or oxypropylenated ethylenediamines, amino acids and the compounds having the following formula:

$$\begin{array}{c} Rx \\ \diagdown \\ N-W-N \\ \diagup \\ Ry \end{array} \begin{array}{c} Rz \\ \diagup \\ \diagdown \\ Rt \end{array}$$

in which W is a $C_1$-$C_6$ alkylene residue optionally substituted with a hydroxyl group or a $C_1$-$C_6$ alkyl radical; Rx, Ry, Rz and Rt, which may be identical or different, represent a hydrogen atom or a $C_1$-$C_6$ alkyl, $C_1$-$C_6$ hydroxyalkyl or $C_1$-$C_6$ aminoalkyl radical.

Examples of such amines that may be mentioned include 1,3-diaminopropane, 1,3-diamino-2-propanol, spermine and spermidine.

The term "alkanolamine" means an organic amine comprising a primary, secondary or tertiary amine function, and one or more linear or branched $C_1$-$C_8$ alkyl groups bearing one or more hydroxyl radicals.

Alkanolamines such as monoalkanolamines, dialkanolamines or trialkanolamines comprising from one to three identical or different $C_1$-$C_4$ hydroxyalkyl radicals are in particular suitable for performing the invention.

Among compounds of this type, mention may be made of monoethanolamine, diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethylamino)methane.

More particularly, the amino acids that may be used are of natural or synthetic origin, in their L, D or racemic form, and comprise at least one acid function more particularly chosen from carboxylic acid, sulfonic acid, phosphonic acid and phosphoric acid functions. The amino acids can be in the neutral or ionic form.

Mention may in particular be made, as amino acids which can be used in the present invention, of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

Advantageously, the amino acids are basic amino acids comprising an additional amine function optionally included in a ring or in a ureido function.

Such basic amino acids are preferably chosen from those corresponding to the following formula:

$$R-CH_2-CH\begin{array}{c} NH_2 \\ \diagup \\ \diagdown \\ CO_2H \end{array}$$

in which R denotes a group chosen from:

$$\begin{array}{c} \text{imidazole ring} \end{array} \quad -(CH_2)_3NH_2 \quad -(CH_2)_2NH_2$$

$$-(CH_2)_2NHCONH_2 \quad -(CH_2)_2NH-\underset{\underset{NH}{\parallel}}{C}-NH_2$$

The compounds corresponding to the above formula are histidine, lysine, arginine, ornithine and citrulline.

The organic amine may also be chosen from organic amines of heterocyclic type. Besides histidine that has already been mentioned in the amino acids, mention may be made in particular of pyridine, piperidine, imidazole, triazole, tetrazole and benzimidazole.

The organic amine can also be chosen from amino acid dipeptides. As amino acid dipeptides that may be used in the present invention, mention may be made especially of carnosine, anserine and balenine.

The organic amine is chosen from compounds comprising a guanidine function. As amines of this type that may be used in the present invention, besides arginine, which has already been mentioned as an amino acid, mention may be made especially of creatine, creatinine, 1,1-dimethylguanidine, 1,1-diethylguanidine, glycocyamine, metformin, agmatine, N-amidinoalanine, 3-guanidinopropionic acid, 4-guanidinobutyric acid and 2-([amino(imino)methyl]amino)ethane-1-sulfonic acid.

Mention may be made in particular of guanidine carbonate or monoethanolamine hydrochloride as hybrid compounds.

More particularly, the dye composition used in the process of the invention contains, as alkaline agent, aqueous ammonia and/or at least one alkanolamine and/or at least one basic amino acid, more advantageously aqueous ammonia and/or at least one alkanolamine. Preferably, the alkaline agent is chosen from aqueous ammonia and monoethanolamine, or a mixture thereof.

Advantageously, the dye composition has a content of alkaline agent(s) ranging from 0.01% to 30% by weight, preferably from 0.1% to 20% by weight and better still from 1% to 10% by weight relative to the weight of the said dye composition. It should be noted that this content is expressed as $NH_3$ in the case where the alkaline agent is aqueous ammonia.

Surfactants

The dye composition may also comprise one or more surfactants.

In particular, the additional surfactant(s) are chosen from anionic, amphoteric, zwitterionic, cationic and nonionic surfactants, and preferentially nonionic surfactants.

The term "anionic surfactant" means a surfactant comprising, as ionic or ionizable groups, only anionic groups. These anionic groups are preferably chosen from the groups —C(O)OH, —C(O)O—, —SO$_3$H, —S(O)$_2$O—, —OS(O)$_2$OH, —OS(O)$_2$O—, —P(O)OH$_2$, —P(O)$_2$O—, —P(O)O$_2$—, —P(OH)$_2$, =P(O)OH, —P(OH)O—, =P(O) O—, =POH and =PO—, the anionic parts comprising a cationic counterion such as an alkali metal, an alkaline-earth metal or an ammonium.

As examples of anionic surfactants that may be used in the dye composition according to the invention, mention may be made of alkyl sulfates, alkyl ether sulfates, alkylamido ether sulfates, alkylarylpolyether sulfates, monoglyceride sulfates, alkylsulfonates, alkylamidesulfonates, alkylarylsulfonates, α-olefin sulfonates, paraffin sulfonates, alkylsulfosuccinates, alkylether sulfosuccinates, alkylamide sulfosuccinates, alkylsulfoacetates, acylsarcosinates, acylglutamates, alkylsulfosuccinamates, acylisethionates and N-acyltaurates, salts of alkyl monoesters of polyglycoside-polycarboxylic acids, acyllactylates, D-galactoside uronic acid salts, alkyl ether carboxylic acid salts, alkylaryl ether carboxylic acid salts, alkylamido ether carboxylic acid salts, and the corresponding non-salified forms of all these compounds, the alkyl and acyl groups of all these compounds comprising from 6 to 40 carbon atoms and the aryl group denoting a phenyl group.

These compounds can be oxyethylenated and then preferably comprise from 1 to 50 ethylene oxide units.

The salts of $C_6$-$C_{24}$ alkyl monoesters of polyglycoside-polycarboxylic acids can be chosen from $C_6$-$C_{24}$ alkyl polyglycoside-citrates, $C_6$-$C_{24}$ alkyl polyglycoside-tartrates and $C_6$-$C_{24}$ alkyl polyglycoside-sulfosuccinates.

When the anionic surfactant(s) are in salt form, they may be chosen from alkali metal salts such as sodium or potassium salt and preferably sodium salt, ammonium salts, amine salts and in particular amino alcohol salts or alkaline-earth metal salts such as magnesium salts.

Examples of amino alcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Alkali metal or alkaline-earth metal salts, and in particular sodium or magnesium salts, are preferably used.

Use is preferably made, among the anionic surfactants mentioned, of ($C_6$-$C_{24}$)alkyl sulfates, ($C_6$-$C_{24}$)alkyl ether sulfates comprising from 2 to 50 ethylene oxide units, in particular in the form of alkali metal, ammonium, amino alcohol and alkaline-earth metal salts, or a mixture of these compounds.

In particular, it is preferable to use ($C_{12}$-$C_{20}$)alkyl sulfates, ($C_{12}$-$C_{20}$)alkyl ether sulfates comprising from 2 to 20 ethylene oxide units, in particular in the form of alkali metal, ammonium, amino alcohol and alkaline-earth metal salts, or a mixture of these compounds. Better still, it is preferred to use sodium lauryl ether sulfate containing 2.2 mol of ethylene oxide.

The amphoteric or zwitterionic surfactant(s), which are preferably (a) non-silicone surfactant(s), which can be used in the present invention may in particular be derivatives of optionally quaternized secondary or tertiary aliphatic amines, in which derivatives the aliphatic group is a linear or branched chain comprising from 8 to 22 carbon atoms, the said amine derivatives comprising at least one anionic group, such as, for example, a carboxylate, sulfonate, sulfate, phosphate or phosphonate group. Mention may be made in particular of ($C_8$-$C_{20}$)alkylbetaines, sulfobetaines, ($C_8$-$C_{20}$)alkylamido($C_3$-$C_8$)alkylbetaines and ($C_8$-$C_{20}$)alkylamido($C_6$-$C_8$)alkylsulfobetaines.

Among the optionally quaternized secondary or tertiary aliphatic amine derivatives that may be used, as defined above, mention may also be made of the compounds having the respective structures (B1) and (B2) below:

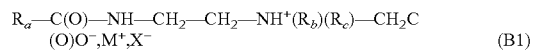

R$_a$—C(O)—NH—CH$_2$—CH$_2$—NH$^+$(R$_b$)(R$_c$)—CH$_2$C
(O)O$^-$,M$^+$,X$^-$ (B1)

in which formula:
R$_a$ represents a $C_{10}$-$C_{30}$ alkyl or alkenyl group derived from an acid R$_a$—COOH preferably present in hydrolysed coconut oil, or a heptyl, nonyl or undecyl group;
R$_b$ represents a β-hydroxyethyl group; and
R$_c$ represents a carboxymethyl group;
M$^+$ represents a cationic counterion derived from an alkali metal or alkaline-earth metal, such as sodium, an ammonium ion or an ion derived from an organic amine; and
X$^-$ represents an organic or inorganic anionic counterion, such as that chosen from halides, acetates, phosphates, nitrates, ($C_1$-$C_4$)alkyl sulfates, ($C_1$-$C_4$)alkyl- or ($C_1$-$C_4$) alkylarylsulfonates, in particular methyl sulfate and ethyl sulfate; or alternatively M$^+$ and X$^-$ are absent;

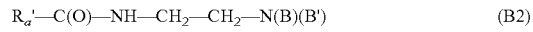

R$_a$'—C(O)—NH—CH$_2$—CH$_2$—N(B)(B') (B2)

in which formula:
B represents the group —CH$_2$—CH$_2$—O—X';
B' represents the group —(CH$_2$)$_z$Y', with z=1 or 2;
X' represents the group —CH$_2$—C(O)OH, —CH$_2$—C(O) OZ, —CH$_2$—CH$_2$—C(O)OH, —CH$_2$—CH$_2$—C(O) OZ, or a hydrogen atom;
Y' represents the group —C(O)OH, —C(O)OZ', —CH$_2$—CH(OH)—SO$_3$H or the group —CH$_2$—CH (OH)—SO$_3$—Z';
Z' represents a cationic counterion derived from an alkali metal or alkaline-earth metal, such as sodium, an ammonium ion or an ion derived from an organic amine;
R$_a$' represents a $C_{10}$-$C_{30}$ alkyl or alkenyl group of an acid R$_a$'—C(O)OH preferably present in coconut oil or in hydrolysed linseed oil, an alkyl group, especially of $C_{17}$ and its iso form, or an unsaturated $C_{17}$ group.

These compounds of formula (B1) or (B2) are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid and cocoamphodipropionic acid.

By way of example, mention may be made of the cocoamphodiacetate sold by the company Rhodia under the trade name Miranol® C2M Concentrate.

Use may also be made of compounds of formula (B'2):

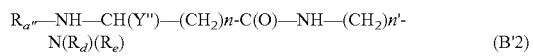
$R_{a''}$—NH—CH(Y'')—(CH$_2$)n-C(O)—NH—(CH$_2$)n'-N(R$_d$)(R$_e$)  (B'2)

in which formula:

Y'' represents the group —C(O)OH, —C(O)OZ'', —CH$_2$—CH(OH)—SO$_3$H or the group —CH$_2$—CH(OH)—SO$_3$—Z'';

$R_d$ and $R_e$, independently of each other, represent a $C_1$-$C_4$ alkyl or hydroxyalkyl radical;

Z'' represents a cationic counterion derived from an alkali metal or alkaline-earth metal, such as sodium, an ammonium ion or an ion derived from an organic amine;

$R_{a''}$ represents a $C_{10}$-$C_{30}$ alkyl or alkenyl group of an acid $R_{a''}$C(O)OH preferably present in coconut oil or in hydrolysed linseed oil.

n and n' denote, independently of each other, an integer ranging from 1 to 3.

Among the compounds of formula (B'2), mention may be made of the compound classified in the CTFA dictionary under the name sodium diethylaminopropyl cocoaspartamide and sold by the company Chimex under the name Chimexane HB.

Among the amphoteric or zwitterionic surfactants mentioned above, use is preferably made of ($C_8$-$C_{20}$)alkylbetaines such as cocoylbetaine, ($C_8$-$C_{20}$)alkylamido($C_3$-$C_8$) alkylbetaines such as cocoylamidopropylbetaine, and the compounds of formula (B'2) such as the sodium salt of diethylaminopropyl laurylaminosuccinamate (INCI name: sodium diethylaminopropyl cocoaspartamide), and mixtures thereof. More preferentially, the amphoteric or zwitterionic surfactant(s) are chosen from cocamidopropylbetaine, cocoylbetaine, the sodium salt of diethylaminopropyl cocoaspartamide (INCI name: sodium diethylaminopropyl cocoaspartamide), and mixtures thereof.

The cationic surfactant(s) that may be used in the dye composition according to the invention comprise, for example, salts of optionally polyoxyalkylenated primary, secondary or tertiary fatty amines, quaternary ammonium salts, and mixtures thereof.

Examples of quaternary ammonium salts that may especially be mentioned include:

those corresponding to the general formula (B3) below:

in which formula:

$R_8$ to $R_{11}$, which may be identical or different, represent a linear or branched aliphatic group comprising from 1 to 30 carbon atoms, or an aromatic group such as aryl or alkylaryl, it being understood that at least one of the groups $R_8$ to $R_{11}$ comprises from 8 to 30 carbon atoms and preferably from 12 to 24 carbon atoms; and X⁻ represents an organic or inorganic anionic counterion, such as that chosen from halides, acetates, phosphates, nitrates, ($C_1$-$C_4$)alkyl sulfates, ($C_1$-$C_4$)alkyl or ($C_1$-$C_4$) alkylaryl sulfonates, in particular methyl sulfate and ethyl sulfate.

The aliphatic groups of $R_8$ to $R_{11}$ may also comprise heteroatoms especially such as oxygen, nitrogen, sulfur and halogens.

The aliphatic groups of $R_8$ to $R_{11}$ are chosen, for example, from $C_1$-$C_{30}$ alkyl, $C_1$-$C_{30}$ alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_{12}$-$C_{22}$)alkyl acetate and $C_1$-$C_{30}$ hydroxyalkyl groups, X⁻ is an anionic counterion chosen from the group of halides, phosphates, acetates, lactates, ($C_1$-$C_4$)alkyl sulfates and ($C_1$-$C_4$) alkyl- or ($C_1$-$C_4$)alkylarylsulfonates.

Among the quaternary ammonium salts of formula (B3), preference is given firstly to tetraalkylammonium chlorides, for instance dialkyldimethylammonium or alkyltrimethylammonium chlorides in which the alkyl group comprises approximately from 12 to 22 carbon atoms, in particular behenyltrimethylammonium chloride, distearyldimethylammonium chloride, cetyltrimethylammonium chloride, benzyldimethylstearylammonium chloride, or else, secondly, distearoylethylhydroxyethylmethylammonium methosulfate, dipalmitoylethylhydroxyethylammonium methosulfate or distearoylethylhydroxyethylammonium methosulfate, or else, lastly, palmitylamidopropyltrimethylammonium chloride or stearamidopropyldimethyl(myristyl acetate)ammonium chloride, sold under the name Ceraphyl® 70 by the company Van Dyk;

quaternary ammonium salts of imidazoline, for instance those of formula (B4) below:

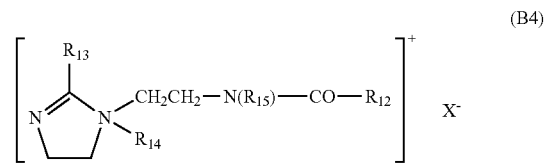

in which formula:

$R_{12}$ represents an alkenyl or alkyl group comprising from 8 to 30 carbon atoms, for example fatty acid derivatives of tallow;

$R_{13}$ represents a hydrogen atom, a $C_1$-$C_4$ alkyl group or an alkenyl or alkyl group comprising from 8 to 30 carbon atoms;

$R_{14}$ represents a $C_1$-$C_4$ alkyl group;

$R_{15}$ represents a hydrogen atom or a $C_1$-$C_4$ alkyl group;

X⁻ represents an organic or inorganic anionic counterion, such as that chosen from halides, phosphates, acetates, lactates, ($C_1$-$C_4$)alkyl sulfates, ($C_1$-$C_4$)alkyl or ($C_1$-$C_4$) alkylaryl sulfonates.

$R_{12}$ and $R_{13}$ preferably denote a mixture of alkyl or alkenyl groups containing from 12 to 21 carbon atoms, for example tallow fatty acid derivatives, $R_{14}$ denotes a methyl group, and $R_{15}$ denotes a hydrogen atom. Such a product is sold, for example, under the name Rewoquat® W 75 by the company Rewo;

quaternary diammonium or triammonium salts, in particular of formula (B5) below:

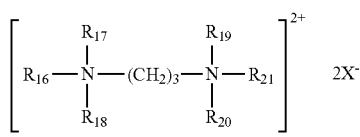

in which formula:
R$_{16}$ denotes an alkyl group comprising approximately from 16 to 30 carbon atoms, which is optionally hydroxylated and/or interrupted with one or more oxygen atoms;
R$_{17}$ is chosen from hydrogen, an alkyl group comprising from 1 to 4 carbon atoms or a group —(CH$_2$)$_3$—N$^+$(R$_{16a}$)(R$_{17a}$)(R$_{18a}$), X$^-$;
R$_{16a}$, R$_{17a}$, R$_{18a}$, R$_{18}$, R$_{19}$, R$_{20}$ and R$_{21}$, which may be identical or different, are chosen from hydrogen and an alkyl group comprising from 1 to 4 carbon atoms; and
X$^-$, which may be identical or different, represent an organic or inorganic anionic counterion, such as that chosen from halides, acetates, phosphates, nitrates, (C$_1$-C$_4$)alkyl sulfates, (C$_1$-C$_4$)alkyl or (C$_1$-C$_4$)alkylaryl sulfonates, in particular methyl sulfate and ethyl sulfate.

Such compounds are, for example, Finquat CT-P, sold by the company Finetex (Quaternium 89), and Finquat CT, sold by the company Finetex (Quaternium 75);

quaternary ammonium salts containing one or more ester functions, such as those of formula (B6) below:

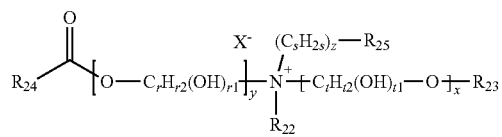

in which formula:
R$_{22}$ is chosen from C$_1$-C$_6$ alkyl groups and C$_1$-C$_6$ hydroxyalkyl or C$_1$-C$_6$ dihydroxyalkyl groups,
R$_{23}$ is chosen from:
  the group

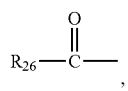

linear or branched, saturated or unsaturated C$_1$-C$_{22}$ hydrocarbon-based groups R$_{27}$,
  a hydrogen atom,
R$_{25}$ is chosen from:
  the group

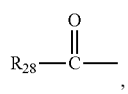

linear or branched, saturated or unsaturated C$_1$-C$_6$ hydrocarbon-based groups R$_{29}$,
  a hydrogen atom, R$_{24}$, R$_{26}$ and R$_{28}$, which are identical or different, are chosen from linear or branched, saturated or unsaturated C$_7$-C$_{21}$ hydrocarbon groups;
r, s and t, which may be identical or different, are integers ranging from 2 to 6,
r1 and t1, which may be identical or different, are equal to 0 or 1, with r2+r1=2r and t1+t2=2t,
y is an integer ranging from 1 to 10,
x and z, which may be identical or different, are integers ranging from 0 to 10,
X$^-$ represents an organic or inorganic anionic counterion, with the proviso that the sum x+y+z equals from 1 to 15, that, when x is 0, then R$_{23}$ denotes R$_{27}$ and that, when z is 0, then R$_{25}$ denotes R$_{29}$.

The alkyl groups R$_{22}$ may be linear or branched, and more particularly linear.

Preferably, R$_{22}$ denotes a methyl, ethyl, hydroxyethyl or dihydroxypropyl group, and more particularly a methyl or ethyl group.

Advantageously, the sum x+y+z is from 1 to 10.

When R$_{23}$ is an R$_{27}$ hydrocarbon-based group, it may be long and may contain from 12 to 22 carbon atoms, or may be short and may contain from 1 to 3 carbon atoms.

When R$_{25}$ is an R$_{29}$ hydrocarbon-based group, it preferably contains 1 to 3 carbon atoms.

Advantageously, R$_{24}$, R$_{26}$ and R$_{28}$, which are identical or different, are selected from linear or branched, saturated or unsaturated C$_{11}$-C$_{21}$ hydrocarbon-based groups, and more particularly from linear or branched, saturated or unsaturated C$_{11}$-C$_{21}$ alkyl and alkenyl groups.

Preferably, x and z, which may be identical or different, are equal to 0 or 1.

y is advantageously equal to 1.

Preferably, r, s and t, which may be identical or different, equal 2 or 3, and even more particularly are equal to 2.

The anionic counterion X$^-$ is preferably a halide, such as chloride, bromide or iodide; a (C$_1$-C$_4$)alkyl sulfate or a (C$_1$-C$_4$)alkyl- or (C$_1$-C$_4$)alkylarylsulfonate. However, it is possible to use methanesulfonate, phosphate, nitrate, tosylate, an anion derived from an organic acid, such as acetate or lactate, or any other anion that is compatible with the ammonium containing an ester function.

The anionic counterion X$^-$ is even more particularly chloride, methyl sulfate or ethyl sulfate.

Use is made more particularly in the dye composition according to the invention of the ammonium salts of formula (B6) in which:
R$_{22}$ denotes a methyl or ethyl group,
x and y are equal to 1,
z is equal to 0 or 1,
r, s and t are equal to 2,
R$_{23}$ is chosen from:
  the group

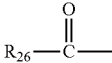

methyl, ethyl or C$_{14}$-C$_{22}$ hydrocarbon-based groups,
  a hydrogen atom,
R$_{25}$ is chosen from:
  the group

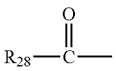

a hydrogen atom,
R$_{24}$, R$_{26}$ and R$_{28}$, which may be identical or different, are chosen from linear or branched, saturated or unsaturated $C_{13}$-$C_{17}$ hydrocarbon-based groups, and preferably from linear or branched, saturated or unsaturated $C_{13}$-$C_{17}$ alkyl and alkenyl groups.

Advantageously, the hydrocarbon-based radicals are linear.

Among the compounds of formula (B6), examples that may be mentioned include salts, especially the chloride or methyl sulfate, of diacyloxyethyldimethylammonium, diacyloxyethylhydroxyethylmethylammonium, monoacyloxyethyldihydroxyethylmethylammonium, triacyloxyethylmethylammonium or monoacyloxyethylhydroxyethyldimethylammonium, and mixtures thereof. The acyl groups preferably contain 14 to 18 carbon atoms and originate more particularly from a plant oil such as palm oil or sunflower oil. When the compound contains several acyl groups, these groups may be identical or different.

These products are obtained, for example, by direct esterification of triethanolamine, triisopropanolamine, an alkyldiethanolamine or an alkyldiisopropanolamine, which are optionally oxyalkylenated, with fatty acids or with fatty acid mixtures of plant or animal origin, or by transesterification of the methyl esters thereof. This esterification is followed by a quaternization by means of an alkylating agent such as an alkyl halide, preferably methyl or ethyl halide, a dialkyl sulfate, preferably dimethyl or diethyl sulfate, methyl methanesulfonate, methyl para-toluenesulfonate, glycol chlorohydrin or glycerol chlorohydrin.

Such compounds are sold, for example, under the names Dehyquart® by the company Henkel, Stepanquat® by the company Stepan, Noxamium® by the company Ceca or Rewoquat® WE 18 by the company Rewo-Witco.

The dye composition according to the invention may contain, for example, a mixture of quaternary ammonium monoester, diester and triester salts with a weight majority of diester salts.

It is also possible to use the ammonium salts containing at least one ester function that are described in patents U.S. Pat. No. 4,874,554 and U.S. Pat. No. 4,137,180.

Use may be made of behenoylhydroxypropyltrimethylammonium chloride sold by KAO under the name Quatarmin BTC 131.

Preferably, the ammonium salts containing at least one ester function contain two ester functions.

Among the cationic surfactants that may be present in the dye composition according to the invention, it is more particularly preferred to choose cetyltrimethylammonium, behenyltrimethylammonium and dipalmitoylethyl-hydroxyethylmethylammonium salts, and mixtures thereof, and more particularly behenyltrimethylammonium chloride, cetyltrimethylammonium chloride, and dipalmitoylethylhydroxyethylammonium methosulfate, and mixtures thereof.

Examples of nonionic surfactants that may be used in the dye composition used according to the invention are described, for example, in the Handbook of Surfactants by M. R. Porter, published by Blackie & Son (Glasgow and London), 1991, pp. 116-178. They are especially chosen from alcohols, α-diols and ($C_1$-$C_{20}$)alkylphenols, these compounds being etherified with ethoxylated, propoxylated and/or glycerolated groups, and containing at least one fatty chain comprising, for example, from 8 to 18 carbon atoms, it being possible for the number of ethylene oxide and/or propylene oxide groups to range especially from 1 to 100, more particularly from 2 to 50, and for the number of glycerol groups to range especially from 1 (problem with the glycerolated groups illustrated) to 30.

Mention may also be made of copolymers of ethylene oxide and propylene oxide, optionally oxyethylenated fatty acid esters of sorbitan, fatty acid esters of sucrose, oxyalkylenated fatty acid esters, optionally oxyalkylenated alkyl polyglycosides, alkyl glucoside esters, derivatives of N-alkyl glucamine and of N-acyl methylglucamine, aldobionamides and amine oxides.

The nonionic surfactants are more particularly chosen from oxyalkylenated or glycerolated nonionic surfactants. The oxyalkylene units are more particularly oxyethylene or oxypropylene units, or a combination thereof, preferably oxyethylene units.

Examples of oxyalkylenated or glycerolated nonionic surfactants that may be mentioned include:
  oxyalkylenated ($C_8$-$C_{24}$)alkylphenols;
  saturated or unsaturated, linear or branched, oxyalkylenated or glycerolated $C_8$-$C_{30}$ alcohols;
  saturated or unsaturated, linear or branched, oxyalkylenated $C_8$-$C_{30}$ amides;
  esters of saturated or unsaturated, linear or branched, $C_8$-$C_{30}$ acids and of polyethylene glycols;
  oxyethylenated esters of saturated or unsaturated, linear or branched $C_8$-$C_{30}$ acids and of sorbitol;
  saturated or unsaturated oxyethylenated vegetable oils;
  condensates of ethylene oxide and/or of propylene oxide, inter alia, alone or as mixtures;
  oxyethylenated and/or oxypropylenated silicones.

The surfactants contain a number of moles of ethylene oxide and/or of propylene oxide ranging from 1 to 100, preferably from 2 to 50 and preferably from 2 to 30. Advantageously, the nonionic surfactants do not comprise any oxypropylene units.

In accordance with a preferred embodiment of the invention, the oxyalkylenated nonionic surfactants are chosen from oxyethylenated $C_8$-$C_{30}$ alcohols comprising from 1 to 100 mol of ethylene oxide; oxyethylenated esters of linear or branched, saturated or unsaturated $C_8$-$C_{30}$ acids and of sorbitol comprising from 1 to 100 mol of ethylene oxide.

As examples of glycerolated nonionic surfactants, glycerolated $C_8$-$C_{40}$ alcohols are preferably used.

Examples of compounds of this type that may be mentioned include lauryl alcohol containing 4 mol of glycerol (INCI name: Polyglyceryl-4 Lauryl Ether), lauryl alcohol containing 1.5 mol of glycerol, Oleyl alcohol containing 4 mol of glycerol (INCI name: Polyglyceryl-4 Oleyl Ether), Oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

Among the glycerolated alcohols, it is more particularly preferred to use the $C_8$/$C_{10}$ alcohol containing 1 mol of glycerol, the $C_{10}$/$C_{12}$ alcohol containing 1 mol of glycerol and the $C_{12}$ alcohol containing 1.5 mol of glycerol.

Preferably, the surfactant(s) are chosen from nonionic, anionic and amphoteric surfactants. More particularly, the surfactant(s) present in the composition are chosen from nonionic surfactants.

Preferably, the surfactant(s), when they are present, are chosen from oxyalkylenated, particularly oxyethylenated, oxypropylenated or glycerolated, nonionic surfactants, or a combination thereof, more particularly oxyethylenated or glycerolated, or mixtures thereof.

Even more preferentially, the nonionic surfactants are chosen from oxyethylenated sorbitol esters, oxyethylenated fatty alcohols, oxyethylenated amides and glycerolated fatty alcohols, and mixtures thereof.

In the dye composition, the amount of surfactant(s), when they are present, preferably ranges from 0.1% to 50% by weight and better still from 0.5% to 20% by weight relative to the total weight of the said composition.

Medium

The medium of the dye composition according to the invention is advantageously an aqueous medium. It may also comprise one or more additional organic solvents other than the above-mentioned $C_6$-$C_{12}$ branched polyol(s).

Examples of organic solvents that may be mentioned include linear or branched and preferably saturated monoalcohols comprising 2 to 10 carbon atoms, linear and preferably saturated diols comprising from 2 to 10 carbon atoms, branched and preferably saturated diols comprising less than 6 carbon atoms or more than 12 carbon atoms, such as ethyl alcohol, isopropyl alcohol, neopentyl glycol, butylene glycol, dipropylene glycol and propylene glycol; aromatic alcohols such as benzyl alcohol or phenylethyl alcohol; linear and preferably saturated polyols comprising from 2 to 10 carbon atoms or branched polyols comprising less than 6 carbon atoms or more than 12 carbon atoms, containing more than two hydroxyl functions, such as glycerol; polyol ethers, for instance ethylene glycol monomethyl, monoethyl or monobutyl ether, propylene glycol or ethers thereof, for instance propylene glycol monomethyl ether; and also diethylene glycol alkyl ethers, especially $C_1$-$C_4$ alkyl ethers, for instance diethylene glycol monoethyl ether or monobutyl ether, alone or as a mixture.

The organic solvents, when they are present, generally represent between 1% and 40% by weight relative to the total weight of the dye composition, and preferably between 5% and 30% by weight relative to the total weight of the dye composition.

The dye composition is preferably aqueous. In this case, it preferably comprises from 30% to 95% by weight of water, better still from 40% to 90% by weight of water and even better still from 50% to 85% by weight of water relative to the total weight of the dye composition.

The pH of the dye composition, if it is aqueous, is generally between 3 and 12 and preferably between 5 and 11. Preferentially between 7 and 11, limits included.

It may be adjusted to the desired value by means of acidifying or basifying agents usually used in the dyeing of keratin fibres, and in particular the alkaline agents of the invention mentioned above.

Fatty Substances

The dye composition contains at least on liquid fatty substance, i.e. a compound that is liquid at a temperature of 25° C. and at atmospheric pressure (also called "oil").

The term "fatty substance" means an organic compound that is insoluble in water at ordinary temperature (25° C.) and at atmospheric pressure (760 mmHg) (solubility of less than 5%, preferably less than 1% and even more preferentially less than 0.1%). They exhibit, in their structure, at least one hydrocarbon chain comprising at least 6 carbon atoms or a sequence of at least two siloxane groups. In addition, the fatty substances are generally soluble in organic solvents under the same temperature and pressure conditions, for instance chloroform, dichloromethane, carbon tetrachloride, ethanol, benzene, toluene, tetrahydrofuran (THF), liquid petroleum jelly or decamethylcyclopentasiloxane.

The fatty substances of the invention do not contain any salified or unsalified carboxylic acid groups (COOH or COO—).

Particularly, the fatty substances of the invention are neither (poly)oxyalkylenated nor (poly)glycerolated.

The term "non-silicone oil" means an oil not containing any silicon atoms (Si) and the term "silicone oil" means an oil containing at least one silicon atom.

More particularly, the liquid fatty substances are chosen from $C_6$-$C_{16}$ hydrocarbons, hydrocarbons containing more than 16 carbon atoms, particularly linear or branched hydrocarbons of mineral or synthetic origin having more than 16 carbon atoms, non-silicone oils of animal origin, plant oils of triglyceride type, synthetic triglycerides, fluoro oils, liquid fatty alcohols, liquid fatty acid and/or liquid fatty alcohol esters other than triglycerides and plant waxes, silicones oils, and mixtures thereof.

It is recalled that the fatty alcohols, esters and acids more particularly have at least one linear or branched, saturated or unsaturated hydrocarbon-based group comprising 6 to 30 and better still from 8 to 30 carbon atoms, which is optionally substituted, in particular with one or more hydroxyl groups (in particular 1 to 4). If they are unsaturated, these compounds may comprise one to three conjugated or unconjugated carbon-carbon double bonds.

As regards the $C_6$-$C_{16}$ hydrocarbons, they are linear, branched or optionally cyclic, and are preferably alkanes. Examples that may be mentioned include hexane, dodecane and isoparaffins such as isohexadecane and isodecane.

A hydrocarbon-based oil of animal origin that may be mentioned is perhydrosqualene.

The triglyceride oils of plant or synthetic origin are preferably chosen from liquid fatty acid triglycerides containing from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by the company Stéarineries Dubois or those sold under the names Miglyol® 810, 812 and 818 by the company Dynamit Nobel, jojoba oil and shea butter oil.

The linear or branched hydrocarbons of mineral or synthetic origin having more than 16 carbon atoms are preferably chosen from liquid paraffins, petroleum jelly, liquid petroleum jelly, polydecenes or hydrogenated polyisobutene, such as Parleam®.

The fluoro oils that may be chosen from perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name Foralkyl® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

The liquid fatty alcohols which are suitable for the implementation of the invention are more particularly chosen from saturated or unsaturated, linear or branched alcohols comprising from 6 to 30 carbon atoms and preferably from 8 to 30 carbon atoms. Mention may be made, for example, of octyldodecanol, 2-butyloctanol, 2-hexyldecanol, 2-undecylpentadecanol, oleyl alcohol or linoleyl alcohol.

As regards the liquid fatty acids, mention may be made especially of saturated or unsaturated carboxylic acids comprising from 6 to 30 carbon atoms, and preferably from 9 to 30 carbon atoms, preferably chosen from oleic acid, linoleic acid, linolenic acid and isostearic acid. Theses acids are not under the form of salts, i.e. if present, the composition may not contain organic or mineral alkaline agents such as sodium hydroxide, potassium hydroxide, monoethanolamine, triethanolamine As regards the liquid esters of a fatty acid and/or of fatty alcohols, which are advantageously different from the triglycerides mentioned previously, mention may be made especially of liquid esters of saturated or unsaturated, linear or branched $C_1$-$C_{26}$ aliphatic monoacids or polyacids and of saturated or unsaturated, linear or branched $C_1$-$C_{26}$ aliphatic monoalcohols or polyalcohols, the total carbon number of the esters being greater than or equal to 6 and more advantageously greater than or equal to 10.

Among the monoesters, mention may be made of; isocetyl stearate; isodecyl neopentanoate; isostearyl neopentanoate; 2-ethylhexyl isononanoate; ethyl and isopropyl palmitates, alkyl myristates such as isopropyl, ethyl, myristate.

Still within the context of this variant, esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxy alcohols may also be used.

Mention may be made especially of: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

Among the esters mentioned above, it is preferred to use ethyl, isopropyl, myristyl, cetyl or stearyl palmitate, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isononyl isononanoate or cetyl octanoate.

The composition may also comprise, as liquid fatty ester, sugar esters and diesters of $C_6$-$C_{30}$ and preferably $C_{12}$-$C_{22}$ fatty acids. It is recalled that the term "sugar" means oxygen-bearing hydrocarbon-based compounds which have several alcohol functions, with or without aldehyde or ketone functions, and which comprise at least 4 carbon atoms. These sugars can be monosaccharides, oligosaccharides or polysaccharides.

Mention may be made, as suitable sugars, for example, of sucrose (or saccharose), glucose, galactose, ribose, fucose, maltose, fructose, mannose, arabinose, xylose and lactose, and derivatives thereof, in particular alkyl derivatives, such as methyl derivatives, for instance methylglucose.

The sugar esters of fatty acids may be chosen in particular from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may comprise one to three conjugated or unconjugated carbon-carbon double bonds.

The esters according to this variant may also be chosen from mono-, di-, tri- and tetraesters, polyesters, and mixtures thereof.

These esters can, for example, be oleates, laurates, palmitates, myristates, behenates, cocoates, stearates, linoleates, linolenates, caprates, arachidonates or mixtures thereof, such as, in particular, oleate/palmitate, oleate/stearate or palmitate/stearate mixed esters.

More particularly, use is made of monoesters and diesters and in particular mono- or di-oleate, -stearate, -behenate, -oleate/palmitate, -linoleate, -linolenate or -oleate/stearate of sucrose, of glucose or of methylglucose.

An example that may be mentioned is the product sold under the name Glucate® DO by the company Amerchol, which is a methylglucose dioleate.

The silicones oils that may be used in the dye composition of the present invention are volatile or non-volatile, cyclic, linear or branched silicones, which are unmodified or modified with organic groups, having a viscosity from $5 \times 10^{-6}$ to 2.5 m$^2$/s at 25° C., and preferably $1 \times 10^{-6}$ to 1 m$^2$/s.

Preferably, the silicone is chosen from liquid polydialkylsiloxanes, especially polydimethylsiloxanes (PDMS), and liquid organomodified polysiloxanes comprising at least one functional group chosen from amino groups and alkoxy groups.

Organopolysiloxanes are defined in greater detail in Walter Noll's *Chemistry and Technology of Silicones* (1968), Academic Press. They may be volatile or non-volatile.

When they are volatile, the silicones are more particularly chosen from those having a boiling point of between 60° C. and 260° C., and more particularly still from:

(i) cyclic polydialkylsiloxanes containing from 3 to 7 and preferably from 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide, and Silbione® 70045 V5 by Rhodia, and mixtures thereof.

Mention may also be made of cyclocopolymers of the dimethylsiloxane/methylalkylsiloxane type, such as Volatile Silicone® FZ 3109 sold by the company Union Carbide, of formula:

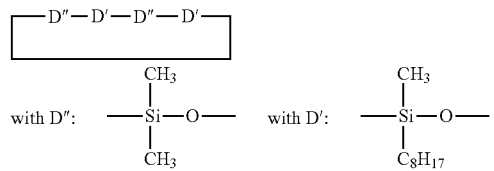

Mention may also be made of mixtures of cyclic polydialkylsiloxanes with organosilicon compounds, such as the mixture of octamethylcyclotetrasiloxane and tetra(trimethylsilyl)pentaerythritol (50/50) and the mixture of octamethylcyclotetrasiloxane and oxy-1,1'-bis(2,2,2',2',3,3'-hexatrimethylsilyloxy)neopentane;

(ii) linear volatile polydialkylsiloxanes containing 2 to 9 silicon atoms and having a viscosity of less than or equal to $5 \times 10^{-6}$ m$^2$/s at 25° C. An example is decamethyltetrasiloxane sold in particular under the name SH 200 by the company Toray Silicone. Silicones belonging to this category are also described in the article published in Cosmetics and Toiletries, Vol. 91, January 76, pp. 27-32, Todd & Byers, *Volatile Silicone Fluids for Cosmetics*.

Use may be made of non-volatile polydialkylsiloxanes, among which mention may be made mainly of polydimethylsiloxanes having trimethylsilyl end groups. The viscosity of the silicones is measured at 25° C. according to ASTM standard 445 Appendix C.

Mention may be made, among these polydialkylsiloxanes, without implied limitation, of the following commercial products:
- the Silbione® oils of the 47 and 70 047 series or the Mirasil® oils sold by Rhodia, such as, for example, the oil 70 047 V 500 000;
- the oils of the Mirasil® series sold by Rhodia;
- the oils of the 200 series from the company Dow Corning, such as DC200 with a viscosity of 60 000 $mm^2/s$;
- the Viscasil® oils from General Electric and certain oils of the SF series (SF 96, SF 18) from General Electric.

Mention may also be made of polydimethylsiloxanes bearing dimethylsilanol end groups known under the name dimethiconol (CTFA), such as the oils of series 48 from the company Rhodia.

The liquid fatty substances are advantageously chosen from $C_6$-$C_{16}$ alkanes, non-silicone oils of plant, mineral or synthetic origin, liquid fatty alcohols, liquid fattu acids and liquid esters of a fatty acid and/or of a fatty alcohol, or mixtures thereof.

Preferably, the liquid fatty substance is chosen from liquid petroleum jelly, $C_6$-$C_{16}$ alkanes, polydecenes, liquid esters of a fatty acid and/or of a fatty alcohol, and liquid fatty alcohols, or mixtures thereof, and preferably from liquid fatty alcohols, more preferably Oleyl alcohol.

The liquid fatty substances are present in an amount of between 0.01% and 20%, preferably 0.5 to 10%, more preferably 0.7 to 5% by weight relative to the weight of the dye composition.

The composition may also contain, in addition to liquid fatty substances, non liquid fatty substances, that may be silicone or non silicone fatty substances, especially pasty or solid fatty substances.

The non silicone non liquid fatty substances may be chosen from waxes, fatty esters, fatty alcohols, more particularly chosen from saturated or unsaturated, linear or branched alcohols comprising from 8 to 30 carbon atoms. Preferably, the fatty alcohol or alcohols are chosen from saturated linear fatty alcohols comprising from 8 to 30 and preferably from 10 to 22 carbon atoms. Mention may be made, for example, of cetyl alcohol, stearyl alcohol, behenyl alcohol and a mixture thereof (cetylstearyl alcohol).

The non-silicone wax(es) are chosen in particular from carnauba wax, candelilla wax, esparto wax, paraffin wax, ozokerite, vegetable waxes, such as olive tree wax, rice wax, hydrogenated jojoba wax or absolute flower waxes, such as the blackcurrant blossom essential wax sold by Bertin (France), or animal waxes, such as beeswaxes or modified beeswaxes (cerabellina); other waxes or waxy starting materials which can be used according to the invention are in particular marine waxes, such as that sold by Sophim under the reference M82, polyethylene waxes or polyolefin waxes in general.

The silicone non liquid fatty substances may be chosen from polydialkylsiloxanes, polydialkylsiloxane gums and resins, polyorganosiloxanes modified with the organofunctional groups, and mixtures thereof.

In the category of polydialkylsiloxanes, mention may also be made of the products sold under the names Abil Wax® 9800 and 9801 by the company Goldschmidt, which are polydi($C_1$-$C_{20}$)alkylsiloxanes.

The silicone gums that may be used in accordance with the invention are in particular polydialkylsiloxanes and preferably polydimethylsiloxanes with high number-average molecular weights of between 200 000 and 1 000 000, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane, tridecane or their mixtures.

Products which can be used more particularly in accordance with the invention are mixtures such as:
- the mixtures formed from a polydimethylsiloxane hydroxylated at the chain end, or dimethiconol (CTFA), and from a cyclic polydimethylsiloxane, also known as cyclomethicone (CTFA), such as the product Q2 1401 sold by Dow Corning;
- the mixtures of a polydimethylsiloxane gum and of a cyclic silicone, such as the product SF 1214 Silicone Fluid from General Electric; this product is an SF 30 gum corresponding to a dimethicone, having a number-average molecular weight of 500 000, dissolved in the oil SF 1202 Silicone Fluid corresponding to decamethylcyclopentasiloxane;
- the mixtures of two PDMSs with different viscosities, and more particularly of a PDMS gum and a PDMS oil, such as the product SF 1236 from General Electric. The product SF 1236 is a mixture of a gum SE 30 defined above, with a viscosity of 20 $m^2/s$, and of an oil SF 96 with a viscosity of $5 \times 10^{-6}$ $m^2/s$. This product preferably comprises 15% of gum SE 30 and 85% of an oil SF 96.

The organopolysiloxane resins that may be used in accordance with the invention are crosslinked siloxane systems containing the following units:

$R_2SiO_{2/2}$, $R_3SiO_{1/2}$, $RSiO_{3/2}$ and $SiO_{4/2}$, in which R represents an alkyl containing 1 to 16 carbon atoms. Among these products, those that are particularly preferred are those in which R denotes a $C_1$-$C_4$ lower alkyl group, more particularly methyl.

Mention may be made, among these resins, of the product sold under the name Dow Corning 593 or those sold under the names Silicone Fluid SS 4230 and SS 4267 by General Electric, which are silicones of dimethyl/trimethylsiloxane structure.

Mention may also be made of the resins of the trimethylsiloxysilicate type, sold especially under the names X22-4914, X21-5034 and X21-5037 by the company Shin-Etsu.

The organomodified silicones that may be used in accordance with the invention are silicones as defined above and comprising in their structure one or more organofunctional groups attached via a hydrocarbon-based group.

In addition to the silicones described above, the organomodified silicones can be polydiarylsiloxanes, in particular polydiphenylsiloxanes, and polyalkylarylsiloxanes functionalized by the abovementioned organofunctional groups.

In a first variant of the invention, the total content of fatty substances (liquid and non liquid) in the mixture, is less than 20% by weight relative to the total weight of the composition (mixture of the dye and oxidizing compositions). It then preferably ranges from a content of more than 0 to 19%, better still from a content of more than 0 to 15% and even better still from a content of more than 0 to 10% by weight relative to the total weight of the composition (mixture of the dye and oxidizing compositions).

In a second variant of the invention, the total content of fatty substances (liquid and non liquid) is greater than or equal to 20% by weight relative to the total weight of the composition (mixture of the dye and oxidizing compositions). It then preferably ranges from 20% to 80%, better still from 30% to 75% and even better still from 50% to 70% by weight relative to the total weight of the composition (mixture of the dye and oxidizing compositions).

Other Adjuvants

The dye composition may also contain various adjuvants, which are conventionally used in hair dye compositions, for instance anionic, cationic, nonionic, amphoteric or zwitterionic polymers or mixtures thereof; thickeners such as crosslinked acrylic acid homopolymers, cellulose-based thickeners (with, for example, hydroxyethylcellulose, hydroxypropylcellulose or carboxymethylcellulose), guar gum and derivatives thereof (for example hydroxypropylguar), gums of microbial origin (especially xanthan gum or scleroglucan gum); mineral thickeners especially such as clays; ammonium salts such as ammonium chloride or ammonium acetate; antioxidants or reducing agents such as ascorbic acid, erythorbic acid, ammonium sulfite, bisulfite or metabisulfite, or ammonium thiolactate; penetrants, sequestrants such as ethylenediaminetetraacetic or salts thereof; fragrances; titanium oxides; buffers; dispersants; and preserving agents, or mixtures thereof.

The above adjuvants are generally present in an amount for each of them of between 0.01% and 20% by weight relative to the weight of the dye composition.

Oxidizing Composition

Chemical Oxidizing Agent

The second composition used in the process according to the invention also comprises at least one chemical oxidizing agent.

It should be noted that the oxidizing agents present in the oxidizing composition are termed "chemical" to distinguish them from atmospheric oxygen.

In particular, the chemical oxidizing agent(s) that are suitable for use in the present invention are chosen, for example, from hydrogen peroxide, urea peroxide, alkali metal bromates or ferricyanides, peroxygenated salts, for instance persulfates, perborates, peracids and precursors thereof and percarbonates of alkali metals or alkaline-earth metals. Advantageously, the oxidizing agent is hydrogen peroxide.

The content of oxidizing agent(s) more particularly represents from 0.1% to 20% by weight and preferably from 0.5% to 10% by weight relative to the weight of the oxidizing composition.

Surfactants

The oxidizing composition may also comprise one or more surfactants which may be chosen from the aforementioned surfactants.

In particular, the surfactant(s) are chosen from anionic, amphoteric, zwitterionic, cationic and nonionic surfactants, and preferentially nonionic surfactants. Reference may be made to the list of compounds of this type given in the context of the description of the dye composition.

Preferably, these surfactants, if they are present, are chosen from nonionic surfactants.

Even more preferably, the oxyalkylenated nonionic surfactants are chosen from oxyethylenated $C_8$-$C_{30}$ alcohols comprising from 1 to 100 mol of ethylene oxide, preferably from 2 to 50 and better still from 2 to 30 mol of ethylene oxide; linear or branched, saturated or unsaturated, $C_8$-$C_{30}$ amides which are non-oxyalkylenated or comprise from 1 to 100 mol of ethylene oxide, preferably from 2 to 50 and better still from 2 to 50 mol of ethylene oxide; oxyethylenated esters of linear or branched, saturated or unsaturated $C_8$-$C_{30}$ acids and of sorbitol comprising from 1 to 100 mol of ethylene oxide.

In the oxidizing composition, the amount of surfactant(s), when they are present, preferably ranges from 0.1% to 50% by weight and better still from 0.5% to 20% by weight relative to the total weight of the said composition.

Medium

The oxidizing composition is advantageously an aqueous composition. It may also comprise one or more additional organic solvents chosen from those listed previously, these solvents more particularly representing, when they are present, from 1% to 40% by weight and preferably from 5% to 30% by weight relative to the weight of the oxidizing composition.

The oxidizing composition also preferably comprises one or more acidifying agents. Among the acidifying agents, examples that may be mentioned include mineral or organic acids, for instance hydrochloric acid, orthophosphoric acid, sulfuric acid, carboxylic acids, for instance acetic acid, tartaric acid, citric acid or lactic acid, and sulfonic acids.

Usually, the pH of the oxidizing composition, when it is aqueous, is less than 7.

Other Adjuvants

The oxidizing composition may also contain various conventionally used adjuvants, for instance anionic, cationic, nonionic, amphoteric or zwitterionic polymers or mixtures thereof; thickeners such as crosslinked acrylic acid homopolymers, cellulose-based thickeners (with, for example, hydroxyethylcellulose, hydroxypropylcellulose or carboxymethylcellulose), guar gum and derivatives thereof (for example hydroxypropylguar), gums of microbial origin (especially xanthan gum or scleroglucan gum); sequestrants such as ethylenediaminetetraacetic or salts thereof; fragrances; and preserving agents, or mixtures thereof.

The above adjuvants are generally present in an amount for each of them of between 0.01% and 20% by weight relative to the weight of the oxidizing composition.

Propellant Gas

As has been indicated previously, the mixture used in the process according to the invention is obtained from at least one pressurized device. In other words, the mixture used in the process according to the invention comprises (initially) one or more propellant gases.

It should be noted that, in the context of the invention, the propellant gas may be employed to enable the expulsion of the composition(s), but also to facilitate or bring about their expansion.

As indicated previously, at least one of the compositions comprises at least one propellant gas, and preferably both the compositions comprise at least one propellant gas. In other words, the gas(es) are mixed with the composition.

As propellant gases that are suitable for use in the invention, mention may be made of the gases usually used in the cosmetic field, in particular optionally halogenated volatile hydrocarbons, for example n-butane, propane, isobutane or pentane, and halogenated derivatives thereof; carbon dioxide, nitrous oxide, dimethyl ether and nitrogen, alone or as mixtures.

Preferably, the propellant gas(es) are chosen from alkanes and in particular from n-butane, propane and isobutane, and mixtures thereof.

The gases are under pressure, more particularly at least partially in liquid form.

In the preferred case in which each of the compositions comprises at least one propellant gas, these gases may be identical or different from one composition to another, whether as regards the nature of the gas(es) or as regards the respective proportions thereof if it is a case of mixtures.

Preferably, the content of propellant gas(es) represents a content ranging from 1% to 30% by weight relative to the weight of the composition, and preferably from 2% to 15% by weight relative to the weight of the composition in which they are present.

Device

The mixture applied to the fibres is thus obtained from the mixing of the dye and oxidizing compositions described previously.

The mixture may be obtained from a single pressurized container comprising either the oxidizing composition or the dye composition as described previously, the said composition being mixed before use with a composition (the dye composition or the oxidizing composition, respectively) obtained from a non-pressurized container such as a bottle or a tube; the mixture of the two compositions comprising at least one branched $C_6$-$C_{12}$ polyol.

The mixture may also be obtained from a single pressurized container comprising the oxidizing composition and the dye composition as described previously in two separate pockets; the mixture of the two compositions comprising at least one branched $C_6$-$C_{12}$ polyol.

Preferably, the mixture used in the context of the invention is obtained from a device comprising:
- a first container containing the dye composition described previously, and
- a second container containing the oxidizing composition also described previously,
- at least one of the containers being pressurized, and preferably both the containers being pressurized;
- a means for dispensing the compositions;
- the mixture of the two compositions comprising at least one branched $C_6$-$C_{12}$ polyol.

Preferably, a means for dispensing each composition is mounted on each container.

One or both the containers may have rigid walls and directly contain the composition.

As a variant, one or both the containers may have rigid walls and include a flexible-walled pocket which contains the composition.

According to this embodiment, either the dye composition is in a pocket, or the oxidizing composition is in a pocket, or both of them are.

According to this configuration, the composition in the pocket may comprise no propellant gas, this gas being located in the volume defined between the rigid walls of the container and the pocket.

Preferably, the composition contained in the pocket comprises itself also at least one propellant gas.

According to another variant, the device comprises a first rigid-walled container which contains one or the other of the dye or oxidizing compositions, the first rigid-walled container including a flexible pocket which itself contains the other of the dye or oxidizing compositions and which constitutes a second container.

Preferably, the device comprises two rigid-walled containers, preferably without a pocket, each containing a composition.

The device comprises a means for dispensing the compositions, the means comprising at least one dispensing valve mounted on the container(s).

Preferably, the means for dispensing the compositions comprises two dispensing valves, each valve being mounted on a container.

The valve(s) are in selective fluid communication with the interior of the container(s) via an inlet orifice of the valve, the communication being established in response to the actuation of an actuating means, such as a push button.

When the device comprises a first rigid-walled container which includes a flexible pocket, only one valve is provided for dispensing the two compositions. The valve is then equipped with two inlet orifices, one of the orifices being able to communicate with the interior of the pocket and the other with the volume defined between the pocket and the rigid walls of the container.

When the containers do not include a pocket, they are equipped with a dip tube for conveying the composition to the inlet orifice of the dispensing valve.

When the containers include a pocket, the valve inlet orifice opens into the pocket.

The device may comprise at least one diffuser which caps the valve(s). According to a first variant, the device comprises a single diffuser which caps the two valves. According to a second variant, the device comprises two diffusers, each independently capping a valve.

The push button may form part of the diffuser.

The diffuser may be equipped with one or more dispensing ducts provided to convey the composition(s) to one or more dispensing orifices.

When the device comprises two diffusers, each of the diffusers is equipped with a duct for conveying the composition between the valve outlet orifice and a dispensing orifice.

When the device comprises a single diffuser, it may be equipped with two ducts for conveying the compositions, each duct communicating with the outlet orifice of a valve.

According to a first embodiment, the two ducts each arrive at a dispensing orifice (not communicating with each other before the dispensing orifice). According to this configuration, the mixing of the compositions does not take place until after they have been dispensed (and thus after the dispensing orifices).

According to a second embodiment, the two ducts arrive in a mixing chamber, from which a single duct is directed towards a single dispensing orifice. According to this configuration, the mixing of the compositions takes place just before the mixture is expelled from the device.

Preferably, the two ducts each open directly onto a dispensing orifice.

When the device comprises two diffusers, namely when it comprises two containers, on each of which is mounted a valve and a diffuser specific thereto, the two containers may be free relative to each other, i.e. not integrally attached.

As a variant, the two containers may be integrally attached, for example by means of an outer envelope partly covering the containers (especially a thermoformed film or a metallic or plasticized rigid envelope), or alternatively by means of notches made in the outer wall of each container, enabling them to be fastened together.

When the device comprises a single diffuser which caps the two valves, this diffuser enables the two containers to be integrally attached. In this case, an outer envelope partly covering the containers may also be envisaged.

In accordance with a particular embodiment of the invention, the device comprises two integrally attached containers, the device enabling the compositions to be dispensed concomitantly, via one or, preferably, two dispensing orifices.

Preferably, according to this embodiment, the containers have rigid walls, a dispensing valve being mounted on each of the containers, a single diffuser capping the two valves.

Needless to say, the devices are designed such that the dye and oxidizing compositions come into contact at the time of application of the mixture obtained.

Mixture

Advantageously, the mixture of the dye composition and of the oxidizing composition, used in the process according to the invention, and which is applied to the fibres, is in the form of a foam, which is thus produced just before it is applied.

More particularly, the dye composition which is dispensed (obtained) from a pressurized container is in the form of a cream, a gel or a foam, preferably in the form of a foam.

Moreover, the oxidizing composition which is dispensed (obtained) from a pressurized container is in the form of a cream, a gel or a foam, preferably in the form of a foam.

The pH of the mixture of the dye and oxidizing compositions is advantageously between 3 and 12, preferably between 5 and 11 and preferentially between 7 and 11, limits inclusive.

It should be noted that the dispensing valve(s), and similarly the content of propellant gas(es), are adapted so as to enable the compositions to be dispensed in suitable respective proportions.

In practice, the dye composition/oxidizing composition weight ratio in the dispensed mixture ranges from 0.25 to 4 and preferably from 0.5 to 2.

Even more preferentially, this ratio is 1.

The dyeing process according to the invention consists in applying the mixture thus obtained to wet or dry human keratin fibres for a time sufficient to develop the desired coloration.

According to the invention, the mixture obtained according to the process of the invention is applied to keratin fibres preferably in the form of a foam.

The dyeing process is generally performed at room temperature (between 15 and 25° C.) and up to temperatures that may be as high as 60° C. to 80° C.

After a leave-on time of from one minute to one hour and preferably from 5 minutes to 30 minutes, the human keratin fibres are rinsed with water, and optionally washed with a shampoo and then rinsed with water.

The example that follows serves to illustrate the invention without, however, being limiting in nature.

EXAMPLE

| Dye composition (contents expressed in g % in native form): | |
|---|---|
| Ingredients | Concentration |
| Oxyethylenated (4 OE) rapeseed acid amide (at 92%, Amidet N sold by the company Kao) | 8.8 |
| Oxyethylenated (3 OE) decyl alcohol (at 90%, Eumulgin BL 309 sold by the company Cognis) | 7.7 |
| Glyceryl C12 alkyl ether (1.5 mol) (Chimexane NV sold by the company Chimex) | 7 |
| Oleyl alcohol | 1.1 |
| Lauryl ether carboxylic acid (4.5 OE) (at 90%, Akypo RLM 45 CA sold by the company Kao) | 5 |
| Monoethanolamine | 3.66 |
| Ethylenediaminetetraacetic acid | 0.2 |
| 96° Ethyl alcohol | 8.8 |
| Propylene glycol | 6.2 |
| Hexylene glycol | 3 |
| Dipropylene glycol | 3 |
| Condensate of ethylene oxide and of propylene oxide and of ethylene oxide (MW: 14 000) (128 OE/54 OP/128 OE) (at 99.95%, Synperonic PE/F 108 (flakes) sold by the company Croda) | 2 |
| Polydimethyldiallylammonium chloride (at 40% in water, Merquat 100 sold by the company Nalco) | 0.1 |

| Dye composition (contents expressed in g % in native form): | |
|---|---|
| Ingredients | Concentration |
| Ammonium thiolactate as an aqueous 58% solution (50% thiolactic acid) | 0.8 |
| Fragrance | 0.95 |
| Erythorbic acid | 0.31 |
| 1,4-Diaminobenzene | 1.45 |
| N,N-Bis(2-hydroxyethyl)-p-phenylenediamine sulfate monohydrate | 0.30 |
| 1,3-Dihydroxybenzene | 0.75 |
| 1-Hydroxy-3-aminobenzene | 0.65 |
| 1-β-Hydroxyethyloxy-2,4-diaminobenzene dihydrochloride | 0.35 |
| Aqueous ammonia (20% concentration of ammonia) | 7 |
| Deionized water | qs |

| Oxidizing composition (contents expressed in g % in native form): | |
|---|---|
| Chemical name | Concentration |
| Mixture of cetylstearyl alcohol/oxyethylenated (33 OE) cetylstearyl alcohol (Sinnowax AO sold by the company Cognis) | 2.85 |
| (50% linear 70/30 $C_{13}/C_{15}$) alkyl ether carboxylic acid monoethanolamide (2 OE) | 0.85 |
| Glycerol | 0.5 |
| Tetrasodium pyrophosphate decahydrate | 0.02 |
| Disodium tin hexahydroxide | 0.04 |
| Diethylenetriaminepentaacetic acid, pentasodium salt as an aqueous 40% solution | 0.15 |
| 50% hydrogen peroxide solution | 12 |
| Phosphoric acid | q.s. for pH 2.2 |
| Deionized water | q.s. for 100 |

Each of the above compositions is conditioned in an aerosol container in the presence of the following propellant gases, in a composition/propellant gases weight ratio of 94/6.

Dye composition: 50% propane, 35% n-butane, 15% i-butane

Oxidizing composition: 25% propane, 40% n-butane, 35% i-butane

The two aerosols are integrally attached via a dispensing head incorporating the two dispensing channels deriving from the two pressurized containers, the mixing of the two compositions in a weight ratio of 1/1 not taking place until immediately after exiting the dispensing head.

The resulting mixture is left on the fibres for 30 minutes at room temperature (25° C.).

A natural shade, which covers grey hair well, is obtained.

The invention claimed is:

1. A process for dyeing keratin fibers comprising:
    (a) preparing a cosmetic mixture by mixing:
        a dye composition comprising at least one oxidation dye precursor and at least one liquid fatty substance, and
        an oxidizing composition comprising at least one chemical oxidizing agent; and
    (b) applying said cosmetic mixture to said keratin fibers;
    wherein the mixture of the two compositions further comprises at least one branched $C_6$-$C_{12}$ polyol;
    wherein the mixture comprises at least one organic solvent other than the at least one branched $C_6$-$C_{12}$ polyol; and
    further wherein at least one of the compositions is dispensed from a pressurized container prior to said mixing.

2. The process according to the claim 1, wherein the at least one branched $C_6$-$C_{12}$ polyol is chosen from compounds of formula (I):

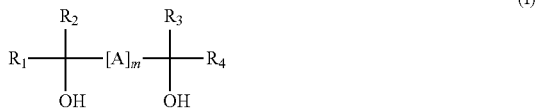

wherein:
$R_1$, $R_2$, $R_3$ and $R_4$ are, independently, chosen from hydrogen atoms, linear $C_1$-$C_6$ alkyl radicals, branched $C_3$-$C_6$ alkyl radicals, or $C_1$-$C_6$ monohydroxyalkyl or polyhydroxyalkyl radicals;
A is chosen from optionally mono- or polyhydroxylated linear $C_1$-$C_{10}$ alkylene radicals or branched $C_3$-$C_{10}$ alkylene radicals, wherein said radicals are optionally interrupted with 1 to 3 oxygen atoms; and
m is equal to 0 or 1;
wherein the radicals $R_1$, $R_2$, $R_3$, $R_4$ and A, may optionally be chosen such that the compound of formula (I) is branched and comprises from 6 to 12 carbon atoms.

3. The process according to claim 2, wherein the at least one branched $C_6$-$C_{12}$ polyol is chosen from compounds of formula (I), wherein:
m is equal to zero, and
$R_1$, $R_2$, $R_3$ and $R_4$ are, independently, a hydrogen atom, an optionally mono- or polyhydroxylated linear $C_1$-$C_6$ or branched $C_3$-$C_6$ alkyl radical,
wherein at least one of the radicals are branched or the radicals $R_1$ and $R_2$ and/or the radicals $R_3$ and $R_4$ are other than hydrogen; and
wherein the radicals are such that the compound of formula (I) is branched and comprises 6 to 12 carbon atoms.

4. The process according to claim 2, wherein the at least one branched $C_6$-$C_{12}$ polyol is chosen from compounds of formula (I), wherein:
m is equal to 1,
$R_1$, $R_2$, $R_3$ and $R_4$ are, independently of each other, a hydrogen atom, an optionally mono- or polyhydroxylated linear $C_1$-$C_6$ or branched $C_3$-$C_6$ alkyl radical,
wherein the radicals are such that the compound of formula (I) is branched and comprises 6 to 12 carbon atoms, and
A is an optionally branched $C_1$-$C_6$ alkylene group, optionally interrupted with one or more oxygen atoms.

5. The process according to claim 2, wherein the at least one branched $C_6$-$C_{12}$ polyol is chosen from pinacol, 3-methyl-1,3,5-pentanetriol, 3-methyl-1,5-pentanediol and hexylene glycol.

6. The process according to claim 2, wherein the at least one branched $C_6$-$C_{12}$ polyol is a diol.

7. The process according to claim 1, wherein the at least one branched $C_6$-$C_{12}$ polyol is present in the cosmetic mixture in an amount ranging from about 0.1% to about 50% by weight, relative to the weight of the cosmetic mixture.

8. The process according to claim 1, wherein the at least one liquid fatty substance is chosen from liquid petroleum jelly, $C_6$-$C_{16}$ alkanes, polydecenes, liquid fatty alcohols, liquid esters of a fatty acid and/or of a fatty alcohol, or mixtures thereof.

9. The process according to claim 1, wherein the at least one liquid fatty substance is present in the dye composition in an amount ranging from about 0.01% to about 20% by weight, relative to the weight of the dye composition.

10. The process according to claim 1, wherein the pressurized container comprises at least one propellant gas chosen from optionally halogenated volatile hydrocarbons and halogenated derivatives thereof.

11. The process according to claim 10, wherein the at least one propellant gas is chosen from n-butane, propane, isobutene, pentane, carbon dioxide, nitrous oxide, dimethyl ether, nitrogen, compressed air, and mixtures thereof.

12. The process according to claim 10, wherein the dye composition and the oxidizing composition each comprise at least one propellant gas, which may be the same or different,
wherein the at least one propellant gas is present in an amount ranging from about 1% to about 30%, relative to the weight of the composition in which it is present.

13. The process according to claim 1, wherein the at least one chemical oxidizing agent is chosen from hydrogen peroxide, urea peroxide, alkali metal bromates or ferricyanides, peroxygenated salts and peracids, and precursors thereof.

14. The process according to claim 1, wherein the dye composition further comprises at least one alkaline agent chosen from aqueous ammonia, alkanolamines, amino acids, or mixtures thereof.

15. The process according to claim 14, wherein the at least one alkaline agent is present in the dye composition in an amount ranging from about 0.01% to about 30% by weight, relative to the weight of the dye composition.

16. The process according to claim 1, wherein the dye composition and/or the oxidizing composition further comprises at least one surfactant chosen from cationic, amphoteric, nonionic, or anionic surfactants.

17. The process according to claim 1, wherein the dye composition and the oxidizing composition are each in a different pressurized container, wherein the containers are optionally integrally attached and equipped with at least one dispensing orifices configured to dispense the compositions concomitantly.

18. The process according to claim 1, wherein the mixture of the dye composition and of the oxidizing composition, as dispensed, is in the form of a foam.

19. A device for dispensing a cosmetic mixture for dyeing keratin fibers, said cosmetic mixture comprising:
a dye composition comprising at least one oxidation dye precursor and at least one liquid fatty substance,
an oxidizing composition comprising at least one chemical oxidizing agent, and
at least one branched $C_6$-$C_{12}$ polyol, and
at least one organic solvent other than the at least one branched $C_6$-$C_{12}$ polyol;
said device comprising:
a first container containing the dye composition comprising at least one oxidation dye precursor, and
a second container containing the oxidizing composition comprising at least one chemical oxidizing agent,
wherein at least one of the first and second containers is pressurized and equipped with a component for dispensing the cosmetic mixture of the dye and oxidizing compositions.

* * * * *